(12) United States Patent
Luka et al.

(10) Patent No.: US 8,494,724 B2
(45) Date of Patent: Jul. 23, 2013

(54) MULTI-FUNCTION SENSOR SYSTEM FOR DETECTING RAINFALL AND FOR RECORDING THE SURROUNDINGS OF VEHICLES

(75) Inventors: Juergen Luka, Tamm (DE); Axel Mueller, Pluederhausen (DE)

(73) Assignee: Daimler AG, Stuttgart (DE)

( * ) Notice: Subject to any disclaimer, the term of this patent is extended or adjusted under 35 U.S.C. 154(b) by 464 days.

(21) Appl. No.: 12/682,371

(22) PCT Filed: Sep. 23, 2008

(86) PCT No.: PCT/EP2008/008020
§ 371 (c)(1),
(2), (4) Date: Apr. 9, 2010

(87) PCT Pub. No.: WO2009/049749
PCT Pub. Date: Apr. 23, 2009

(65) Prior Publication Data
US 2010/0241321 A1 Sep. 23, 2010

(30) Foreign Application Priority Data
Oct. 15, 2007 (DE) .......................... 10 2007 049 256

(51) Int. Cl.
*G01S 17/93* (2006.01)
*G01N 21/47* (2006.01)
*G06F 7/00* (2006.01)

(52) U.S. Cl.
USPC ........................................... 701/49; 356/342

(58) Field of Classification Search
USPC ........... 701/49; 356/342, 5.01, 5.08; 362/459, 362/507; 73/170.17
See application file for complete search history.

(56) References Cited

U.S. PATENT DOCUMENTS

| 4,699,507 | A | * | 10/1987 | Etoh | 356/5.08 |
| 5,898,183 | A | * | 4/1999 | Teder | 250/574 |
| 6,097,024 | A | * | 8/2000 | Stam et al. | 250/208.1 |
| 6,108,084 | A | * | 8/2000 | Winner | 356/338 |
| 6,118,383 | A | * | 9/2000 | Hegyi | 340/602 |
| 6,393,377 | B1 | * | 5/2002 | Shirai et al. | 702/159 |
| 6,516,664 | B2 | * | 2/2003 | Lynam | 73/170.17 |
| 6,534,884 | B2 | * | 3/2003 | Marcus et al. | 307/10.1 |

(Continued)

FOREIGN PATENT DOCUMENTS

| DE | 19952552 A1 | 5/2000 |
| DE | 10330526 A1 | 1/2005 |

(Continued)

*Primary Examiner* — Thomas Black
*Assistant Examiner* — Wae Louie
(74) *Attorney, Agent, or Firm* — Patent Central LLC; Stephan A. Pendorf

(57) ABSTRACT

A sensor system and method for detecting particles, in particular dirt particles or water droplets on a vehicle windscreen, comprising an optical sensor (3). The sensor (3) operates on the basis of light transit time and receives light signals (S) that are emitted by an emitter element and that are at least partially reflected, wherein the emitter element and the sensor (3) are located and aligned on the exterior of the vehicle, on or in the vicinity of a tailgate, hatchback or trunk lid (2) of said vehicle (1) in such a way that particles on the tailgate, hatchback or trunk lid (2) can be detected by means of the sensor (3) by sensing the part of light signals (S) emitted by the emitter element that is backscattered by the particles.

17 Claims, 2 Drawing Sheets

U.S. PATENT DOCUMENTS

| | | | |
|---|---|---|---|
| 6,946,639 B2* | 9/2005 | Stam et al. | 250/208.1 |
| 7,199,346 B2* | 4/2007 | Stam et al. | 250/208.1 |
| 7,274,386 B2* | 9/2007 | Pochmuller et al. | 348/135 |
| 7,350,945 B2* | 4/2008 | Albou et al. | 362/507 |
| 7,485,844 B2* | 2/2009 | Stam et al. | 250/227.25 |
| 8,045,760 B2* | 10/2011 | Stam et al. | 382/104 |
| 8,082,783 B2* | 12/2011 | Backes | 73/170.17 |
| 8,134,117 B2* | 3/2012 | Heslin et al. | 250/239 |
| 8,134,692 B2* | 3/2012 | Yamaguchi | 356/5.01 |
| 2005/0180149 A1* | 8/2005 | Albou et al. | 362/459 |
| 2010/0241321 A1* | 9/2010 | Luka et al. | 701/49 |

FOREIGN PATENT DOCUMENTS

| | | |
|---|---|---|
| DE | 102006030639 A1 | 7/2007 |
| EP | 1182105 A | 2/2002 |
| JP | 2006343273 A | 12/2006 |

* cited by examiner

MULTI-FUNCTION SENSOR SYSTEM FOR DETECTING RAINFALL AND FOR RECORDING THE SURROUNDINGS OF VEHICLES

BACKGROUND OF THE INVENTION

1. Field of the Invention

The invention relates to a sensor system, a use of a sensor system, and a method for detecting particles, in particular dirt particles or water droplets on a vehicle windscreen.

2. Description of the Related Art

Sensor systems for the detection of particles of the type mentioned at the outset are also called rain sensors in the state of the art and serve for detecting water droplets or dirt particles on front windscreens of motor vehicles.

With the known sensor systems for the detection of particles, with the known uses of sensor systems, and with the known methods for detecting particles, a sensor is arranged in the vehicle interior at vehicle windscreens, with which water droplets can be detected on the exterior of the vehicle windscreen.

It is thereby disadvantageous that these systems are elaborate and are thus usually only used for vehicle front windscreens. It is further disadvantageous that these known sensor systems are only suitable for the detection of particles.

In addition, from DE 10 2006 030 639 A1 is known a sensor system in the upper region of vehicles, in which the opening and closing paths are monitored by doors or tailgate, hatchback or trunk lids.

It is thereby disadvantageous and when using these sensor systems that these can only be used restricted to doors and tailgate, hatchback or trunk lids.

It is the object of the invention to give an improved sensor system for the detection of particles, an improved use of sensor systems, and an improved method for the detection of particles.

BRIEF SUMMARY OF THE INVENTION

The solution of the object relating to the sensor system is achieved according to the invention by a sensor system for detecting particles, in particular dirt particles or water droplets on a vehicle windscreen, comprising an optical sensor (3), wherein the sensor (3) is based on light transit time, receives light signals (S) that are emitted by an emitter element and that are at least partially reflected, wherein the emitter element and the sensor (3) are located and aligned on the exterior of the vehicle, on or in the vicinity of a tailgate, hatchback or trunk lid (2) of the vehicle (1) in such a way that particles on the tailgate, hatchback or trunk lid (2) can be detected by means of the sensor (3) by sensing the part of light signals (S) emitted by the emitter element that is backscattered by the particles.

The uses of the sensor system and methods for the use of the sensor system are set forth below.

Advantageous arrangements of the invention are the subject of the dependent claims.

The sensor system according to the invention for the detection of particles comprises an optical sensor and is particularly suitable for the detection of dirt particles or water droplets on a vehicle windscreen. According to the invention, the sensor is based on light transit time and receives light signals emitted by an emitter element, and which are and at least partially reflected, wherein the emitter element and the sensor are arranged and aligned at or in the region of a tailgate, hatchback or trunk lid of the vehicle at the exterior of the vehicle in such a manner that particles on the tailgate, hatchback or trunk lid can be detected by sensing a part backscattered at the particles by means of the sensor of the light signals emitted by the emitter element. The sensor monitors the space behind the tailgate, hatchback or trunk lid for this, and senses reflected light signals from water droplets which are present on the tailgate, hatchback or trunk lid. The strength of these sensed light signals is larger than the strength of sensed reflected light signals with a rear windscreen which is free of water droplets and unsoiled. An automatic actuation of a rear windscreen wiper can thereby be triggered. Wiping intervals can additionally be adjusted, or washing functions can be triggered. The sensor system according to the invention can thereby be used as a rain sensor system.

According to one arrangement of the invention, the sensor is a sensor for distance measurement. The sensor system according to the invention can thereby not only be used for the detection of particles on the tailgate, hatchback or trunk lid (rain sensor), but also for monitoring the pivoting range of the tailgate, hatchback or trunk lid (obstacle recognition) and/or for sensing the distance to an obstacle during parking (parking aid) of the vehicle. The sensor of the sensor system according to the invention can thereby be used in a multiple manner, that is, for several purposes.

The choice or the switchover of the current functionality/functionalities to be carried out by the sensor as rain sensor, parking aid and/or for obstacle recognition preferably takes place automatically. In this, if is possible that the choice or the switchover of the functionality/functionalities takes place via characteristic maps. Wherein the characteristic maps can contain parameters about the driver behavior and/or the drive situation. The sensor system functions for example as a rain sensor when driving forward, when reversing, the function as parking aid is active, and when the vehicle is standing or parking, the sensor system is used for obstacle recognition, in particular as impact protection, to thereby monitor the pivoting range of the vehicle tailgate, hatchback or trunk lid.

By the fact that the sensor is based on a light transit time for the distance determination, very exact distance measurements are enabled in a simple manner while using cost-efficient components.

A particularly preferred arrangement of the invention provides that the sensor is arranged integrated into a third brake light of the vehicle. The sensor is thereby not only protected from soiling in an especially effective manner, but it is also protected from mechanical impairment or from a change of its alignment. A correct and defined alignment of the sensor is of particular importance, as a particle detection shall take place on the basis of different strengths of sensed light signals with a rear windscreen which is soiled or covered with water droplets, compared to a rear windscreen which is free of water droplets and which is unsoiled. A threshold of the backscattered part sensed by the sensor of the light signals emitted by the emitter, which is adjusted and/or established and/or determined once only, on the basis of which particles are detected on the tailgate, hatchback or trunk lid, can thereby remain unchanged after a first calibration.

A further preferred arrangement provides that the sensor and the emitter element are one component. Thereby, not only the effort during the assembly of the sensor system is reduced, but it is also ensured that the emission of the light signals remains unchanged in a predetermined direction region and in a certain strength after a first calibration.

Another preferred arrangement of the invention provides that the sensor can also be used for monitoring the pivoting range of the tailgate, hatchback or trunk lid, in particular an electrically operated tailgate, hatchback or trunk lid, besides the particle detection. The sensor system according to the invention can thereby be used for vehicles with electrically operated tailgate, hatchback or trunk lids in a simple manner in that a pivoting movement of the tailgate, hatchback or trunk lid during opening is automatically stopped when detecting an obstacle by means of the sensor. Tailgate, hatchback or trunk lids can thereby be protected efficiently from collisions with objects such as garage door lintels, roofs, beams or other vehicles. It is additionally optionally possible to stop the pivoting movement of the tailgate, hatchback or trunk lid during the closure of the tailgate, hatchback or trunk lid automatically if the sensor or a further sensor monitors the region below the tailgate, hatchback or trunk lid, and an obstacle, in particular a person id detected in this region. Collisions with persons can thereby be prevented and danger of injuries can be reduced.

Another preferred arrangement of the invention provides that, apart from the particle detection, the sensor can also be used for sensing the distance to an obstacle, in particular when parking the vehicle A first alternative for a use of a sensor system, in particular a sensor system according to the invention, provides that a tailgate, hatchback or trunk lid is monitored in such a manner that particles, in particular dirt particles or water droplets are detected on the tailgate, hatchback or trunk lid. The advantages mentioned for the sensor system according to the invention result therewith.

A second alternative for a use of a sensor system, in particular a sensor system according to the invention, provides that the pivoting range of the tailgate, hatchback or trunk lid is monitored for an obstacle, and that, for avoiding a collision of the tailgate, hatchback or trunk lid with the obstacle, the pivoting region of the tailgate, hatchback or trunk lid is limited automatically, or the pivoting movement is automatically stopped when opening or when closing the tailgate, hatchback or trunk lid, if the obstacle is detected in the pivoting range of the tailgate, hatchback or trunk lid. It is thereby achieved in a simple manner to protect the tailgate, hatchback or trunk lid from collisions with objects and/or obstacles such as roof boxes, garage drives with a limited height, walls or other vehicles. This alternative of the use according to the invention is particularly suitable for vehicles with electrically operated tailgate, hatchback or trunk lids, as, in this case, the opening or the closing of the tailgate, hatchback or trunk lid can take place in a simple manner by switching off the drive of the tailgate, hatchback or trunk lid. It is optionally possible to signal the stopping of the pivoting movement of the tailgate, hatchback or trunk lid, in particular by a warning sound and/or an information in a display in the vehicle.

A third alternative for a use of a sensor system, in particular a sensor system according to the invention, provides that the region behind the vehicle is monitored with regard to an obstacle by means of the sensor, wherein the distance to the obstacle is determined, in particular when parking the vehicle. A reversing parking aid can thereby be realized in a simple manner, or a parking aid system of the vehicle can be supplemented.

From the three alternatives for a use of a sensor system, which can also take place simultaneously in pairs, or all three simultaneously, the advantages mentioned for the sensor system according to the invention. The choice from the three alternatives for a use thereby preferably takes place in an automatic manner, in dependence on the drive situation and/or the driver behavior.

The method according to the invention for the detection of particles, which can particularly be used for the detection of dirt particles or water droplets on a vehicle windscreen, provides that light signals emitted and reflected by an emitter element windscreen, provides that light signals emitted and reflected by an emitter element are received by a sensor based on light transit time, which is arranged on the exterior or in the vicinity of a tailgate, hatchback or trunk lid of a vehicle. Particles on the tailgate, hatchback or trunk lid are thereby detected by means of a backscattered part of the light signals emitted by the emitter element sensed by means of the sensor. The method according to the invention is preferably carried out with the sensor system according to the invention. The space behind the tailgate, hatchback or trunk lid is thereby monitored by the sensor by sensing light signals by the sensor, which were reflected by water droplets, which are present on the tailgate, hatchback or trunk lid. The strength of light signals sensed in this manner is larger than the strength of sensed reflected light signals with a rear windscreen which is free of water droplets and which is unsoiled. After the detection of particles on the rear windscreen by means of a certain threshold, an automatic actuation of a rear windscreen wiper can be triggered, wiping intervals can be adjusted, or washing functions can be triggered. Additionally, control signals of the front windscreen wiper of the vehicle can also be considered for the automatic actuation of the rear windscreen wiper according to another arrangement. The rear windscreen wiper can for example also be activated automatically if no particles are detected on the rear windscreen by means of the sensor system, but if the front windscreen wipers are active. Such an arrangement offers additional safety and comfort. Furthermore, further parameters can also be provided in addition to the determined threshold, from which depend the automatic actuation of the rear windscreen wiper and/or the adjustment of wiping intervals and/or the triggering of washing functions. Different values for controlling the rear windscreen wiper and/or a washer system connected thereto can for example be selected by means of the further parameters. One or several values are chosen from a characteristic map for the selection by means of the parameters.

One arrangement of the method according to the invention provides that, by exceeding a certain threshold of the backscattered part of the light signals emitted by the emitter element sensed by the sensor, particles are detected on the tailgate, hatchback or trunk lid. The threshold is determined in such a manner that exceeding it or reaching it already means a detection of particles. The threshold can preferably be adjusted, so that, after the mounting of the sensor, and the emitter element optionally in operation therewith, a calibration is carried out, with which it is determined, from which strength of the backscattered part of the light signals emitted by the emitter element a particle detection shall be present.

BRIEF DESCRIPTION OF THE SEVERAL VIEWS OF THE DRAWINGS

The invention is explained in more detail in the following by means of embodiments.

It shows thereby.

DETAILED DESCRIPTION OF THE INVENTION

Figure 1:
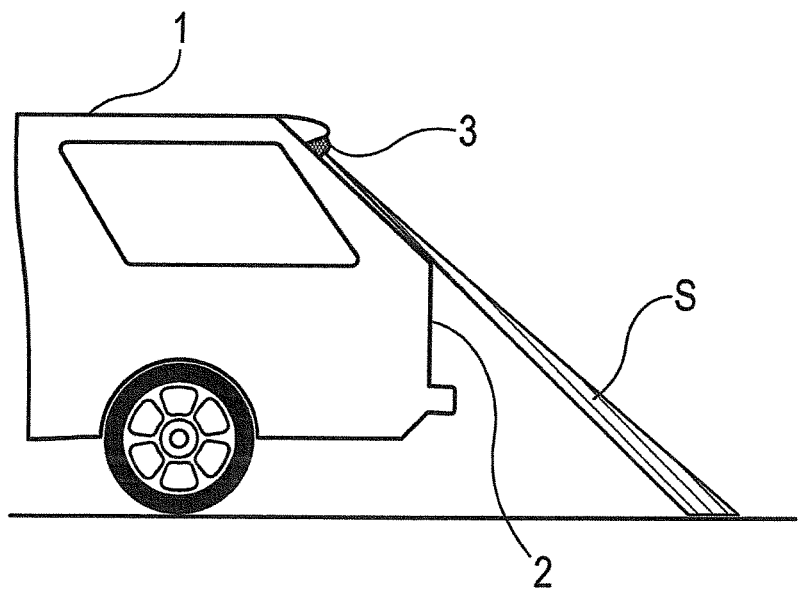
FIG. 1 a schematic representation of the sensor system according to the invention on a vehicle with an unsoiled tailgate, hatchback or trunk lid, FIG. 2 a schematic representation of the sensor system according to the invention on a vehicle with a soiled tailgate, hatchback or trunk lid as a first use according to the invention, FIG. 3a a schematic representation of a first embodiment of a second use of the sensor system according to the invention, FIG. 3b a further schematic representation of the second embodiment of the second use of the sensor system according to the invention, and FIG. 4 a schematic representation of a third use of the sensor system according to the invention.
Figure 2:
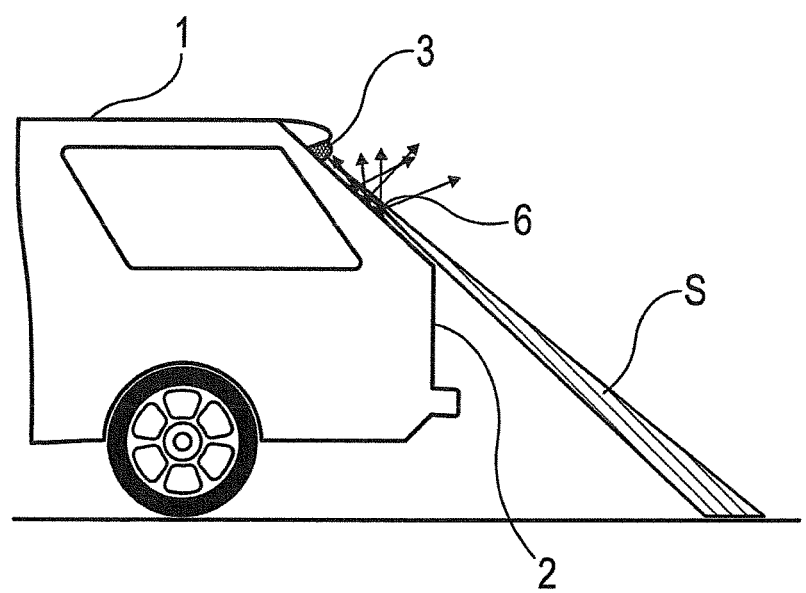

Corresponding parts are provided with the same reference numerals in all figures.

FIG. 1 shows a vehicle 1 with an electrically operable tailgate, hatchback or trunk lid 2 with a third brake light, into which an optical sensor 3 is integrated. The sensor 3 is formed as a distance sensor and can be used on the basis of a light transit time for very exact distance measurements. The sensor 3 is formed with an emitter element for emitting light signals S as a component and is arranged on the exterior of the vehicle 1. In that the sensor 3 is integrated into the emitter element in the third brake light, it is not visible, and is protected from soiling. The sensor 3 measures the distance to objects which reflect light; in the illustrated case to the road. A part of the light signals S emitted by the emitter element is thereby reflected to the road from the unsoiled rear windscreen. The sensor measures a very small part of light signals S reflected at the rear windscreen and the tailgate, hatchback or trunk lid, and which are emitted diffusely by the emitter element. This part of reflected and diffusely emitted light signals S is smaller than an adjusted, determined threshold of a strength of light signals S; thereby, no water droplets or soilings are detected on the rear windscreen.

Figure shows the vehicle 1 described in FIG. 1 with a closed tailgate, hatchback or trunk lid 2. Diverse particles 6, namely water droplets, are on the tailgate, hatchback or trunk lid 2. The sensor 3 monitors the space behind the tailgate, hatchback or trunk lid 2. The sensor 3 senses light signals S reflected by the water droplets; the strength of the light signals S sensed by the sensor 3 is larger than the strength of the reflected light signals S sensed by the sensor 3 with a tailgate, hatchback or trunk lid 2 free of water droplets and dirt. The adjusted, determined threshold of a strength of light signals S is exceeded thereby, so that a detection of particles 6 takes place and an automatic actuation of a rear windscreen wiper, not shown here, can be triggered. The sensor 3 can thereby be used as a rain sensor.

Figures 3A, 3B:
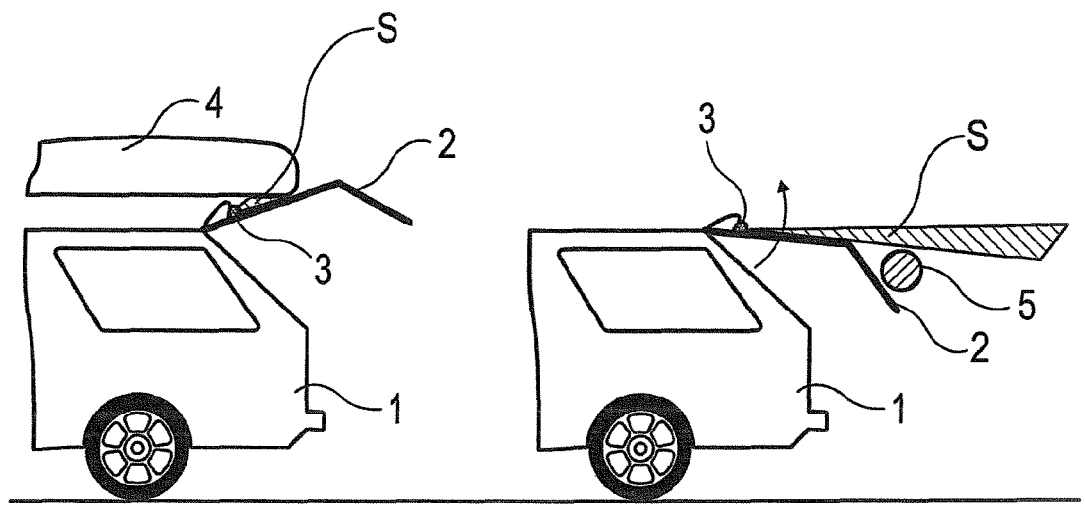

FIG. 3a shows the vehicle 1, which has, in addition to the vehicle described in FIG. 1, a roof box, which is in the usual pivoting range of the tailgate, hatchback or trunk lid 2. The tailgate, hatchback or trunk lid 2 is shown in the opened state. The sensor 3 has monitored the space behind and above the tailgate, hatchback or trunk lid 2 during the electrical opening of the tailgate, hatchback or trunk lid 2; immediately prior to a collision of the tailgate, hatchback or trunk lid 2 with the roof box 4, the further opening of the tailgate, hatchback or trunk lid 2 was interrupted automatically, after the sensor 3 has detected an obstacle, namely the roof box 4 in the immediate vicinity of the tailgate, hatchback or trunk lid 2.

FIG. 3b shows the vehicle 1 described in FIG. 1 with a tailgate, hatchback or trunk lid 2 which is not opened completely. An object 5 is behind the vehicle 1 in the usual pivoting range of the tailgate, hatchback or trunk lid 2. The sensor 3 has monitored the space behind the tailgate, hatchback or trunk lid 2 during the electrical opening of the tailgate, hatchback or trunk lid 2; the further opening of the tailgate, hatchback or trunk lid 2 was interrupted automatically immediately prior to a collision of the tailgate, hatchback or trunk lid 2 with the object 5, after the sensor 3 has detected an obstacle, namely the object 5, in the direct vicinity of the tailgate, hatchback or trunk lid 2.

Figure 4:
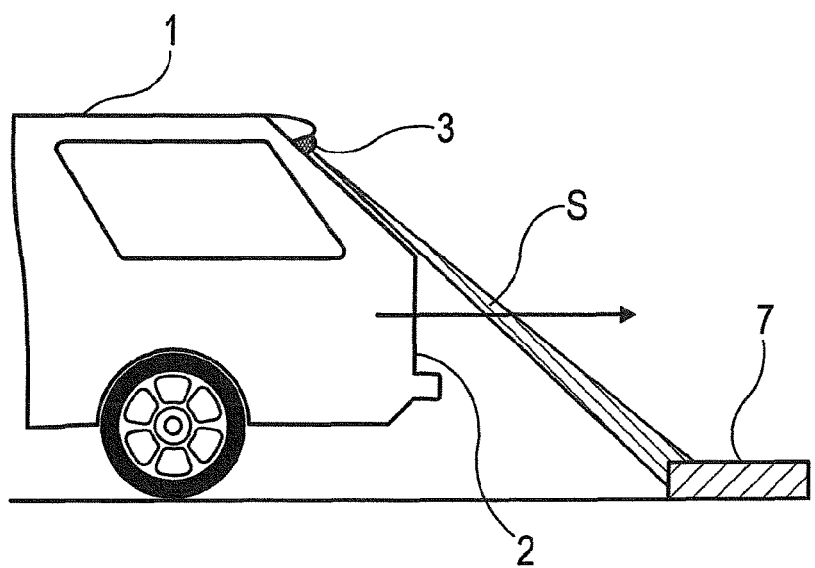

FIG. 4 shows the vehicle 1 described in FIG. 1 with a closed tailgate, hatchback or trunk lid 2. The vehicle 1 moves slowly backwards in a parking operation. The sensor 3 monitors the space behind the tailgate, hatchback or trunk lid 2. The sensor 3 senses light signals 1 reflected from a curbstone 7. A distance between sensor 3 and the curbstone 7 can thereby be measured; the distance between vehicle 1 and the curbstone 7 can be determined therefrom. A warning signal is triggered when a defined distance is undercut. The sensor 3 can thereby be used as a parking aid.

LIST OF REFERENCE NUMERALS

1 Vehicle
2 Tailgate, hatchback or trunk lid
3 Sensor
4 Roof box
5 Object
6 Particle
7 Curbstone
S Light signal

The invention claimed is:

1. A sensor system for detecting particles on a vehicle windscreen, comprising an optical sensor (3), wherein the sensor (3) is based on light transit time, receives light signals (S) that are emitted by an emitter element and that are at least partially reflected, wherein the emitter element and the sensor (3) are located and aligned on the exterior of the vehicle, on or in the vicinity of a tailgate, hatchback or trunk lid (2) of the vehicle (1) in such a way that particles on the tailgate, hatchback or trunk lid (2) can be detected by means of the sensor (3) by sensing the part of light signals (S) emitted by the emitter element that is backscattered by the particles.

2. The sensor system according to claim 1, wherein the sensor (3) is a sensor (3) for distance measurement.

3. The sensor system according to claim 1, wherein the sensor (3) is arranged to be integrated into a third brake light of the vehicle (1).

4. The sensor system according to claim 1, wherein the sensor (3) and the emitter element are one component.

5. The sensor system according to claim 1, wherein the sensor (3) is used for monitoring the pivoting range of the tailgate, hatchback or trunk lid (2).

6. The sensor system according to claim 5, wherein a pivoting movement of the electrically operated tailgate, hatchback or trunk lid (2) can be stopped automatically during the detection of an obstacle by the sensor (3).

7. The sensor system according to claim 1, wherein the sensor (3) is used for sensing the distance to an obstacle.

8. The sensor system according to claim 1, wherein said particles are dirt particles or water droplets.

9. The sensor system according to claim 1, wherein the sensor (3) is used for monitoring the pivoting range of an electrically operated tailgate, hatchback or trunk lid (2).

10. The sensor system according to claim 1, wherein the sensor (3) be is used for sensing the distance to an obstacle when parking the vehicle (1).

11. A method for operating an optical sensor for detecting particles and for sensing the surroundings of a vehicle, wherein the optical sensor (3) is based on light transit time, receives light signals (S) that are emitted by an emitter element and that are at least partially reflected, wherein the emitter element and the sensor (3) are located and aligned on the exterior of the vehicle, on or in the vicinity of a tailgate, hatchback or trunk lid (2) of the vehicle (1) in such a way that particles on the tailgate, hatchback or trunk lid (2) can be detected by means of the sensor (3) by sensing the part of light signals (S) emitted by the emitter element that is backscattered by the particles, said method:

detecting particles on the tailgate, hatchback or trunk lid (2) and in addition at least one of:

monitoring the pivoting range of the tailgate, hatchback or trunk lid (2) with regard to an obstacle, and, for avoiding a collision of the tailgate, hatchback or trunk lid (2) with the obstacle, automatically limiting the pivoting range of the tailgate, hatchback or trunk lid (2) or automatically stopping the pivoting movement during opening or during closing of the tailgate, hatchback or trunk lid (2), if the obstacle is detected in the pivoting range of the tailgate, hatchback or trunk lid (2); and monitoring the region behind the vehicle (1) for an obstacle by means of the sensor (3), wherein the distance to the obstacle is determined when parking the vehicle (1).

12. The method according to claim 11, wherein the optical sensor is operated
in dependence on the drive situation and/or the driver behavior.

13. The method according to claim 11, wherein exceeding a certain threshold of the backscattered part of the light signals (S) emitted by the emitter element sensed by the sensor (3) is interpreted as detection of particles on the tailgate, hatchback or trunklid (2).

14. The method according to claim 13, further comprising adjusting the detection threshold.

15. The method according to claim 13, wherein adjusting the detection threshold results in adjustment of
an automatic actuation of the tailgate, hatchback or trunk lid windscreen wiper wiping intervals, and washing functions.

16. The method according to claim 15, wherein further parameters are evaluated for at least one of the automatic actuation of the rear windscreen wiper, the adjustment of washing intervals, and triggering of washing functions.

17. The method according to claim 11, wherein said particles are dirt particles or water droplets.

* * * * *